United States Patent

Aumüller et al.

Patent Number: 5,821,292
Date of Patent: Oct. 13, 1998

[54] 3-ARYLACRYLIC ACID ESTER LIGHT-PROTECTION STABILIZERS FOR ORGANIC MATERIAL

[75] Inventors: Alexander Aumüller, Neustadt; Martin Holderbaum, Ludwigshafen; Wolfgang Goetze, Maxdorf; Jürgen Krockenberger, Ludwigshafen; Hubert Trauth, Dudenhofen, all of Germany

[73] Assignee: BASF Aktiengesellschaft, Ludwigshafen, Germany

[21] Appl. No.: 836,043

[22] PCT Filed: Nov. 3, 1995

[86] PCT No.: PCT/EP95/04313

§ 371 Date: May 12, 1997

§ 102(e) Date: May 12, 1997

[87] PCT Pub. No.: WO96/15184

PCT Pub. Date: May 23, 1996

[30] Foreign Application Priority Data

Nov. 11, 1994 [DE] Germany ............ 44 40 288.0

[51] Int. Cl.[6] .............. C08K 5/32; C08K 5/18; C08K 5/15; C08K 5/12; C08K 5/10
[52] U.S. Cl. .......... 524/291; 524/108; 524/240; 524/260; 524/285; 524/287; 524/288; 524/290
[58] Field of Search ............. 524/291, 285, 524/287, 108, 240, 288, 260, 290; 560/60; 424/78; 514/972

[56] References Cited

U.S. PATENT DOCUMENTS

| | | | |
|---|---|---|---|
| 2,775,574 | 12/1956 | Slocombe et al. | 524/287 |
| 3,052,636 | 9/1962 | Strobel et al. | 252/300 |
| 3,074,971 | 1/1963 | Strobel et al. | 524/291 |
| 3,085,097 | 4/1963 | Strobel et al. | 524/291 |
| 3,244,668 | 4/1966 | Knapp et al. | 524/291 |
| 3,278,448 | 10/1966 | Laurer et al. | 524/291 |
| 4,049,869 | 9/1977 | Long. | |
| 4,273,833 | 6/1981 | Long. | |
| 4,322,544 | 3/1982 | Okazaki et al. | 560/55 |
| 5,000,945 | 3/1991 | Kobayashi et al. | 514/844 |

FOREIGN PATENT DOCUMENTS

| | | | |
|---|---|---|---|
| 1922815 | 11/1970 | Germany. | |
| A 19 22 815 | 11/1970 | Germany. | |
| 3012535 | 10/1980 | Germany. | |
| A 30 12 535 | 10/1980 | Germany. | |
| A 53 102 357 | 9/1978 | Japan. | |
| A 05 201 928 | 8/1993 | Japan. | |
| A 07 207 063 | 8/1995 | Japan. | |
| 1171888 | 11/1969 | United Kingdom | 524/337 |
| WO 95/23182 | 8/1995 | WIPO. | |

*Primary Examiner*—Veronica P. Hoke
*Attorney, Agent, or Firm*—Oblon, Spivak, McClelland, Maier & Neustadt, P.C.

[57] ABSTRACT

The use of 3-arylacrylic esters I

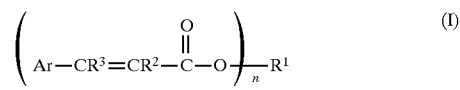

where

Ar is an aryl radical which can additionally carry substituents, $R^1$ is the residue of an n-hydric aliphatic polyol having up to 20 carbon atoms, where the carbon chain can be interrupted by up to 9 non-adjacent oxygen atoms, or of an n-hydric cyclo-aliphatic polyol having 5 to 20 carbon atoms in which ring carbon atoms can also be replaced by non-adjacent oxygen atoms, $R^2$ and $R^3$ are hydrogen or $C_1$–$C_4$-alkyl, and n is a number from 1 to 10, as stabilizers, in particular against the action of light, for non-living organic material.

17 Claims, No Drawings

3-ARYLACRYLIC ACID ESTER LIGHT-PROTECTION STABILIZERS FOR ORGANIC MATERIAL

BACKGROUND OF THE INVENTION

1. Field Of The Invention

The present invention relates to the use of 3-arylacrylic esters of the general formula I $$\left( Ar-CR^3=CR^2-\overset{O}{\underset{\|}{C}}-O \right)_n R^1 \quad (I)$$

where

Ar is an aryl radical which can additionally carry substituents, $R^1$ is the residue of an n-hydric aliphatic polyol having up to 20 carbon atoms, where the carbon chain can be interrupted by up to 9 non-adjacent oxygen atoms, or of an n-hydric cyclo-aliphatic polyol having 5 to 20 carbon atoms in which ring carbon atoms can also be replaced by non-adjacent oxygen atoms, $R^2$ and $R^3$ are hydrogen or $C_1$—$C_4$-alkyl, and n is a number from 1 to 10, as stabilizers, in particular against the action of light, for non-living organic material.

2. Description Of The Background Art

3-Arylacrylic esters of the abovementioned type, for example 2-ethylhexyl p-methoxycinnamate, have been known for a long time in cosmetics for protecting the human skin against the action of light.

The compounds used to date to protect non-living organic material, in particular plastics and surface coatings, have had different chemical structures, for example sterically hindered amines of the polyalkylpiperidine type or benzotriazole derivatives. Agents of this type are intended to combat the damage to organic material which is normally manifested by yellowing or discoloration and embrittlement of the organic material.

Said prior art agents are frequently still unsatisfactory in that their compatibility with plastics is too low, the duration of the protective effect is too short, the substances have an intrinsic color and are volatile, and the stabilizers undergo thermal decomposition on incorporation at elevated temperature.

SUMMARY OF THE INVENTION

It is an object of the present invention to provide stabilizers, in particular against the action of light, which afford more effective protection for organic material. It was particularly intended to increase the duration of the protective effect.

We have found that this object is achieved by using the 3-aryl-acrylic esters I defined at the outset.

In a preferred embodiment, Ar is a phenyl, biphenyl [sic] or naphthyl radical which can be substituted by one to three $C_1$—$C_4$-alkyl groups, $C_1$—$C_4$-alkoxy groups, hydroxyl groups, phenoxy groups, amino groups which can be mono- or disubstituted by $C_1$—$C_4$-alkyl groups, or halogen atoms, nitro groups or a methylene-dioxy group, it being possible for the substituents to be identical or different.

Examples of Ar which may be mentioned are:
phenyl,
o-, m- of p-tolyl,
o-, m- or p-ethylphenyl,
o-, m- or p-propylphenyl,
m- or p-cumyl,
o-, m- or p-butylphenyl,
m- or p-isobutylphenyl,
m- or p-sec-butylphenyl,
m- or p-tert-butylphenyl,
2,3-, 2,4-, 2,5-, 2,6-, 3,4- or 3,5-dimethylphenyl,
mesityl,
o-, m- or p-methoxyphenyl,
o-, m- or p-ethoxyphenyl,
o-, m- or p-propoxyphenyl,
m- or p-isopropoxyphenyl,
o-, m- or p-butoxyphenyl,
m- or p-isobutoxyphenyl,
m- or p-sec-butoxyphenyl,
m- or p-tert-butoxyphenyl,
2,3-, 2,4-, 2,5-, 2,6-, 3,4- or 3,5-dimethoxyphenyl,
o-, m- or p-hydroxyphenyl,
2,3-, 2,4-, 2,5-, 2,6-, 3,4- or 3,5-dihydroxyphenyl,
3-hydroxy-4-methoxyphenyl,
m- or p-phenoxyphenyl,
o-, m- or p-aminophenyl,
o-, m- or p-(N-methylamino)phenyl,
o-, m- or p-(N,N-dimethylamino)phenyl,
o-, m- or p-fluorophenyl,
o-, m- or p-chlorophenyl,
2,4-dichlorophenyl,
o-, m- or p-bromophenyl,
o-, m- or p-nitrophenyl,
2,3- or 3,4-methylenedioxyphenyl,
2-, 3- or 4-biphenyl [sic] and
α- or β-naphthyl.

$C_1$—$C_4$-Alkoxyphenyl radicals are particularly preferred, especially when the alkoxy radical is in the p position on the phenyl nucleus. Among these radicals, attention is drawn particularly to p-methyoxyphenyl.

Where n=1, examples of $R^1$ are the following aliphatic radicals: methyl, ethyl, n-propyl, isopropyl, n-butyl, isobutyl, sec-butyl, tert-butyl, n-pentyl, isopentyl, sec-pentyl, tert-pentyl, neopentyl, n-hexyl, n-heptyl, n-octyl, 2-ethylhexyl, n-nonyl, isononyl, n-decyl, n-undecyl, n-dodecyl, n-tridecyl, isotridecyl, n-tetra-decyl, n-hexadecyl, n-octadecyl, n-eicosyl, vinyl, allyl, methallyl, oleyl, linolyl and linolenyl. Of these, straight-chain or branched $C_5$—$C_{16}$-alkyl groups, in particular straight-chain or branched $C_8$—$C_{12}$-alkyl groups, are preferred. Straight-chain or branched $C_8$-alkyl groups including, in particular, 2-ethylhexyl are of particular interest.

where n=2 to 10, suitable examples of n-valent radicals $R^1$ derived from polyols of the formula $R^1(OH)_n$ are, in particular, those which have 2 to 12 carbon atoms and which can be interrupted in their linear or branched carbon framework by up to 3 non-adjacent oxygen atoms or which can contain individual oxygen atoms in their cyclic carbon framework. A few examples thereof are:

```
CH2—   CH2—   CH2—   CH2—   CH2—   —CH2CH2—O—CH2CH2—
|      |      |      |      |
CH2—   CH—    CH2    CH2    CH—
       |      |      |      |
       CH3    CH2—   CH2    CH2
                     |      |
                     CH2—   CH3

—CH2CH2—O—CH2CH2—O—CH2CH2—   CH2—            CH2—
                             |               |
                             CH—    —CH2—C—
                             |               |
                             CH2—            CH2—
```

-continued

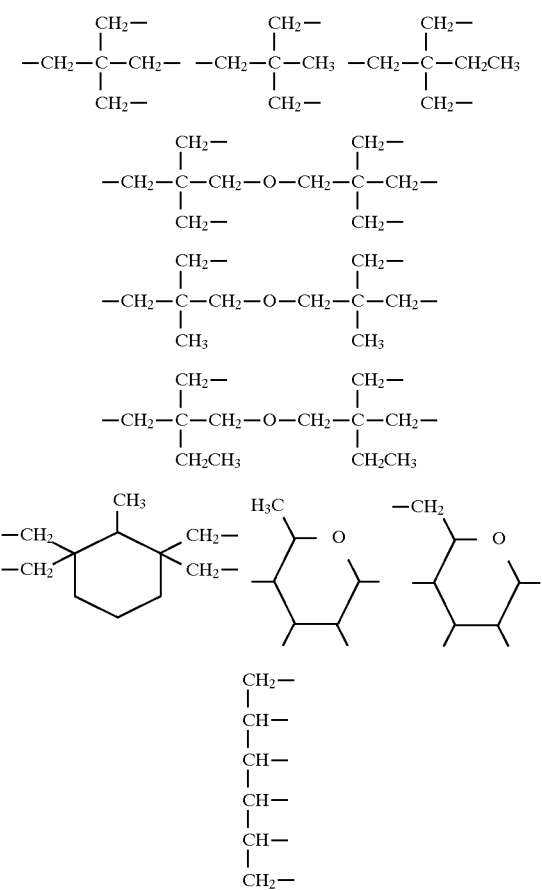

Examples of suitable polyvalent cycloaliphatic radicals are those which are derived from the polyhydric alcohols 1,3-cyclopentanediol, 1,3-cyclohexanediol or, particularly, from 1,4-cyclohexanediol or 1,4-cyclohexanedimethanol, it also being possible for the cycloalkyl rings to be substituted by further alkyl groups.

The variable n is preferably a number from 1 to 6, in particular from 1 to 4, but especially 1 or 2.

The radicals $R^2$ and $R^3$ are, independently of one another, in particular hydrogen, methyl or ethyl. Compounds I where $R^2$ is hydrogen or methyl and $R^3$ is hydrogen are very particularly preferred.

The 3-arylacrylic esters I are outstandingly suitable for stabilizing non-living organic material against the action of light, oxygen and heat. They are also effective as metal deactivators. They are added to the organic material to be stabilized in a concentration of from 0.01 to 5%, preferably from 0.02 to 2%, of the weight of the organic material, before, during or after its production.

Non-living organic material means, for example, cosmetic products such as ointments and lotions, pharmaceutical formulations such as pills and suppositories, photographic recording materials, especially photographic emulsions, or precursors for plastics and surface coatings, but especially plastics and surface coatings themselves.

The present invention also relates to non-living organic material stabilized against the action of light, oxygen and heat, especially plastics and surface coatings, which contains one or more compounds I in the abovementioned concentrations.

The compounds I can be mixed in particular with plastics using all known equipment and methods for mixing stabilizers or other additives into polymers.

The non-living organic material stabilized by the compounds I may also contain further additives, eg. antioxidants, light stabilizers, metal deactivators, antistatic agents, flame retardants, pigments and fillers.

Antioxidants and light stabilizers which can be added beside the compounds I are, for example, compounds based on sterically hindered phenols, sterically hindered amines, chroman derivatives or sulfur- or phosphorus-containing costabilizers.

Examples of phenolic antioxidants which may be mentioned are 2,6-di-tert-butyl-4-methylphenol, n-octadecyl β-(3,5-di-tert-butyl-4-hydroxyphenyl) propionate, 1,1,3-tris (2-methyl-4-hydroxy-5-tert-butylphenyl) butane, 1,3,5-trimethyl-2,4,6-tris (3,5-di-tert-butyl-4-hydroxybenzyl) benzene, 1,3,5-tris(3,5-di-tert-butyl-4-hydroxybenzyl) isocyanurate, 1,3,5-tris[β-(3,5-di-tert-butyl-4-hydroxybenzyl)propionylethyl] isocyanurate, 1,3,5-tris(2,6-dimethyl-3-hydroxy-4-tert-butylbenzyl) isocyanurate and pentaerythritol tetrakis[β-3,5-di-tert-butyl-4-hydroxyphenyl) propionate] [sic].

Examples of suitable phosphorus-containing antioxidants are tris(nonylphenyl) phosphite, distearyl pentaerythritol diphosphite, tris(2,4-di-tert-butylphenyl) phosphite, distearyl pentaerythritol diphosphite [sic], tris(2-tert-butyl-4-methylphenyl) phosphite, bis(2,4-di-tert-butylphenyl) pentaerythritol diphosphite and tetrakis(2,4-di-tert-butylphenyl) 4,4'-biphenylene diphosphite.

Examples of sulfur-containing antioxidants which may be mentioned are dilauryl thiodipropionate, dimyristyl thiodipropionate, distearyl thiodipropionate, pentaerythritol tetrakis-β-laurylthiopropionate) [sic] and pentaerythritol tetrakis(–β-hexylthiopropionate). It is furthermore possible to add thiobisphenols such as 3,3'-di-tert-butyl-4,4'-dihydroxy-2,2'-dimethyldiphenyl sulfide.

Examples of further antioxidants and light stabilizers which can be used together with the compounds I are 2-(2-hydroxyphenyl)-benzotriazoles, 2-hydroxybenzophenones, aryl esters of hydroxybenzoic acids, α-cyanocinnamic acid derivatives, benzimidazole-carboxanilides, nickel compounds or oxanilides.

Particularly effective stabilization is obtained when at least One other light stabilizer from the class of sterically hindered amines is added in the usual concentration in addition to compounds I.

Examples of further sterically hindered amines suitable for this purpose are: bis(2,2,6,6-tetramethylpiperidyl) sebacate, bis(1,2,2,6,6-pentamethylpiperidyl) sebacate, the condensate of 1-hydroxyethyl-2,2,6,6-tetramethyl-4-hydroxypiperidine with succinic acid, the condensate of N,N'-(2,2,6,6-tetramethylpiperidyl) hexamethylenediamine with 4-tert-octylamino-2,6-di-chloro-1,3,5-triazine, tris(2,2,6,6-tetramethylpiperidyl) nitrilotriacetate, tetrakis(2,2,6,6-tetramethy-4-piperidyl)-1,2,3,4-butanetetracarboxylic acid [sic], 1,11-(1,2-ethanediyl)-bis (3,3,5,5-tetramethylpiperazinone), and the condensates of 4-amino-2,2,6,6-tetramethylpiperidines with tetramethylolacetylene-diureas.

Particularly effective stabilization of polyurethanes is obtained when a sterically hindered amine, eg. bis(2,2,6,6-tetramethylpiperidyl) sebacate or bis(1,2,2,6,6-pentamethylpiperidyl) sebacate and, in addition, a mixture of a chroman derivative (vitamin E, α-tocopherol), an organic phosphate and an amine as described in German Patent Application P 44 05 670.2 are added, in the usual concentration, in addition to the compounds I.

A mixture of the compounds I with a sterically hindered amine and a chroman derivative is also suitable and particularly advantageous for stabilizing plastics, especially polyurethanes.

Examples of plastics and thermosets which can be stabilized by the compounds I are:

polymers of mono- and diolefins such as low- and high-density polyethylene, polypropylene, linear poly-1-butene, polyisoprene, polybutadiene, and copolymers of mono- or diolefins or mixtures of said polymers;

copolymers of mono- or diolefins with other vinyl monomers such as ethylene/alkyl acrylate copolymers, ethylene/alkyl methacrylate copolymers, ethylene/vinyl acetate copolymers or ethylene/ acrylic acid copolymers;

polystyrene and copolymers of styrene or α-methylstyrene with dienes and/or acrylic derivatives such as styrene/butadiene, styrene/acrylonitrile (SAN), styrene/ethyl methacrylate, styrene/ butadiene/ethyl acrylate, styrene/acrylonitrile/methacrylate, acrylonitrile/butadiene/styrene (ABS) or methyl methacrylate/ butadiene/styrene (MBS);

halogenated polymers such as polyvinyl chloride, polyvinyl fluoride, polyvinylidene fluoride and copolymers thereof;

polymers derived from α,β unsaturated acids and derivatives thereof, such as polyacrylates, polymethacrylates, polyacrylamides and polyacrylonitriles;

polymers derived from unsaturated alcohols andamines or their acrylic derivatives or acetals, eg. polyvinyl alcohol and polyvinyl acetate;

polyurethanes, polyamides, polyureas, polyphenylene ethers, polyesters, polycarbonates, polyoxymethylenes, polysulfones, polyether sulfones and polyether ketones.

It is furthermore possible to stabilize surface coatings with the compounds I, eg. industrial coatings. Among these, particular emphasis is placed on stoved coatings, and among these in turn on automotive coatings, preferably two-layer coatings.

The compounds I can be added in solid or dissolved form to the coating agent. Their good solubility in coating systems is a particular advantage in this connection.

The compounds I are preferably used to stabilize polyurethanes, especially polyurethane foams, but also polyurethane moldings, polycarbonates and automotive coatings, especially in the automobile sector.

The compounds I are distinguished by being very compatible with conventional types of plastic and having good solubility and excellent compatibility in conventional coating systems. They are stable and nonvolatile at conventional plastic- and surface coating-processing temperatures. Particular advantages which may be emphasized over known stabilizers are that the compounds I to be used according to the invention have distinctly less intrinsic color and thus have virtually no effect on the neutral shade of, especially, transparent plastics such as polycarbonates, polymethylmethacrylate and polyesters, polyurethane foams and surface coatings. In addition, the compounds I used according to the invention have an improved stabilizing effect, ie. in their presence the material begins to deteriorate much later.

EXAMPLES OF USE

EXAMPLE 1

(Polycarbonate)

0.20 part by weight of 2-ethylhexyl p-methoxycinnamate (A) was incorporated into 100 parts by weight of polycarbonate (Macrolon®PC 2800 from Bayer) by a single extrusion at 280° C., and the resulting granules were converted into test specimens 2 mm thick in an injection molding machine at 300° C.

The test specimens produced in this way were tested for their light- and weather-resistance in a Xenotest® 1200 accelerated weathering machine. The aging was determined by measuring the ASTM D 1925 yellowness index after defined time intervals. The illumination time did not exceed 2,000 hours in any of the tests.

For comparison with the prior art, the benzotriazole derivative of the formula B was incorporated in the same way in the same amounts into the same polycarbonate and tested in the same way.

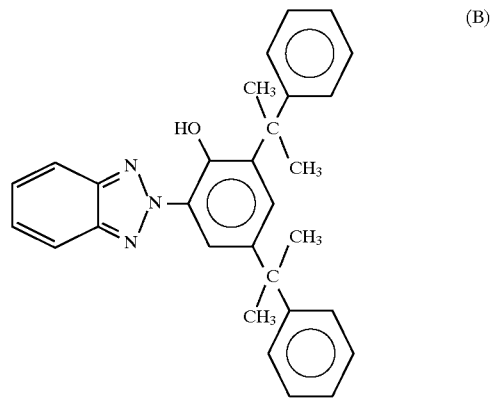

(B)

The results are compiled in Table 1.

TABLE 1

| Stabilizer | Yellowness index after hours (Xenotest 1200) | | | |
|---|---|---|---|---|
|  | 0 | 1000 | 1500 | 2000 |
| No stabilizer | 10.3 | 15.5 | 20.1 | 21.8 |
| A (according to the invention) | 10.2 | 11.0 | 14.2 | 15.3 |
| B (comparative) | 11.5 | 12.7 | 15.6 | 16.8 |

EXAMPLE 2

(Polyurethane Foam)

(Preparation Of The Illumination Samples):

A polyol component comprising 41.9 g of a polyetherol (OH number: 29.0) which had been obtained by addition of propylene oxide and ethylene oxide onto propylene glycol and contained approximately 84% by weight primary hydroxyl groups, 42.5 g of a polyetherol (OH number: 27.0) which had been obtained by addition of propylene oxide and ethylene oxide onto trimethylolpropane and contained approximately 88% by weight primary hydroxyl groups, 8.1 g of 1,4-butanediol, 1.724 g of a 25% by weight solution of diazabicyclooctane in 1,4-butanediol, 0.016 g of dibutyltin dilaurate, 0.1 g of the silicone stabilizer OS 710 from Bayer, 5.49 g of fluorotrichloromethane and 0.17 ml of water were mixed with the stabilizers specified below (0.5 g of each) and foamed to test sheets in the ratio of 100:48.5 by weight with a prepolymer which had 23.0% by weight isocyanate groups at 25° C. (component and tool temperature). The NCO prepolymer in this case had been prepared from 87.17 g of 4,41-diphenylmethane diisocyanate, 4.83 g of a polyetherol (OH number: 250) which was obtained by addition of propylene oxide onto propylene glycol, and 8.0 g of dipropylene glycol.

The compound used according to the invention was compound A from Example 1. Compound C obtained from the two stated components was used for comparison with the prior art.

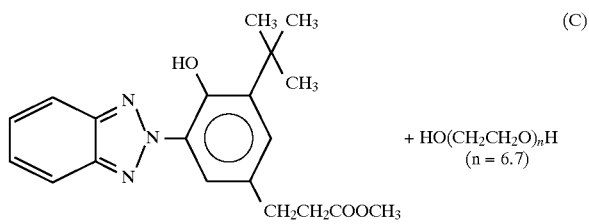

The test sheets were illuminated in a Xenotest 450 and then the ASTM D 1925 yellowness index was determined. The results are shown in Table 2.

TABLE 2

| Stabilizer | Yellowness index after hours (Xenotest 450) | |
| --- | --- | --- |
| | 0 | 240 |
| No stabilizer | 2.8 | 45.2 |
| A (according to the invention) | 3.0 | 17.0 |
| C (comparative) | 3.4 | 18.4 |

EXAMPLE 3

0.5% by weight of the compound

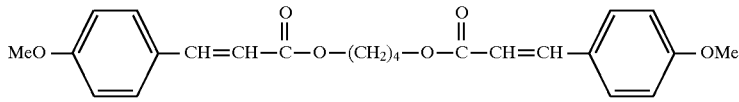

were dissolved together with 0.5 % by weight of N,N'-bis (2,2,6,6-tetramethyl-4-piperidinyl)-N,N'-bisformyl-1,6-diaminohexane by extrusion once in white acrylonitrile/butadiene/styrene copolymer (ABS) at 250° C. (based on the total amount of copolymer). The resulting granules were injection molded at 260° C. to give articles 2 mm thick. The moldings were examined for their lightfastness in an accelerated light-exposure instrument (Xenotest 450 type). The yellowing caused by photooxidative degradation of the polymer was measured. The yellowing was expressed by the yellowness index YI determined in accordance with US standard ASTM D 1925. A high index means severe yellowing.

In parallel with the example compounds, the known UV absorber ethyl 2-cyano-3,3-diphenylacrylate was incorporated as comparative example in the same concentration together with the sterically hindered piperidine in ABS. Table 3 shows the yellowing behavior of the example compound compared with the UV absorber used in a known manner.

EXAMPLE 4

0.5% by weight of the compound

were extruded together with 0.5% by weight of N,N'-bis-(2,2,6,6-tetramethyl-4-piperidinyl)-N,N'-bisformyl-1,6-diaminohexane in ABS and investigated in an accelerated light-exposure test as in Example 3. The result is shown in Table 3.

TABLE 3

| Stabilizer | Yellowness index after hours (Xenotest 450) | | |
| --- | --- | --- | --- |
| | 0 hours | 1000 hours | 400 hours at 90° C. |
| Comparative example | 18.5 | 21.0 | 30.0 |
| Example 3 | 19.0 | 19.7 | 29.8 |
| Example 4 | 18.9 | 19.5 | 26.9 |

We claim:
1. A method of stabilizing a polyurethane polymer comprising combining said polyurethane with at least one 3-arylacrylic ester of the formula I:

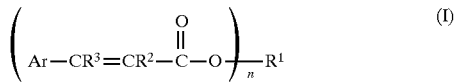

where
Ar is an aryl radical, optionally substituted by one to three $C_1$–$C_4$-alkyl groups, $C_1$–$C_4$-alkoxy groups, hydroxyl groups, phenoxy groups, amino groups which can be mono- or disubstituted by $C_1$–$C_4$-alkyl groups, or halogen atoms, nitro groups or a methylenedioxy group, said substituents being identical or different,
$R^1$ is the residue of an n-hydric aliphatic mono- or polyol having, up to 20 carbon atoms, where the carbon chain can be interrupted by up to 9 non-adjacent ether oxygen atoms, or of an n-hydric cyclo-aliphatic polyol having 5 to 20 carbon atoms in which ring carbon atoms can also be replaced by non-adjacent ether oxygen atoms,
$R^2$ and $R^3$ are each, independently, hydrogen or $C_1$–$C_4$-alkyl, and
n is a number from 1 to 10.
2. The method as claimed in claim 1, where Ar is a $C_1$—$C_4$-alkoxyphenyl radical.
3. The method as claimed in claim 1, where Ar is p-methoxyphenyl.
4. The method as claimed in claim 1, where $R^1$ is the residue of a straight-chain or branched aliphatic polyol having 5 to 16 carbon atoms.
5. The method as claimed in claim 1, wherein n is 1 and $R^1$ is 2-ethylhexyl.
6. The method as claimed in claim 1, where $R^2$ is hydrogen or methyl and $R_3$ is hydrogen.
7. The method as claimed in claim 1, where n is 1.
8. The method as claimed in claim 1, wherein said polyurethane is coated on a surface to form a coating.

9. A composition comprising:
a polyurethane or polycarbonate polymer; and
0.01 to 5% by weight, based on the weight of said organic material, of a 3-arylacrylic ester of formula I:

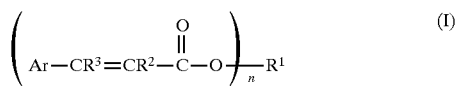 (I)

where
- Ar is an aryl radical optionally substituted by one to three $C_1$—$C_4$-alkyl groups, $C_1$—$C_4$-alkoxy groups, hydroxyl groups, phenoxy groups. amino groups which can be mono- or disubstituted by $C_1$—$C_4$-alkyl groups, or halogen atoms, nitro groups or a methylenedioxy group said substituents being identical or different.
- $R^1$ is the residue of an n-hydric aliphatic polyol having up to 20 carbon atoms, where the carbon chain can be interrupted by up to 9 non-adjacent ether oxygen atoms, or of an n-hydric cyclo-aliphatic polyol having 5 to 20 carbon atoms in which ring carbon atoms can also be replaced by non-adjacent ether oxygen atoms,
- $R^2$ and $R^3$ are each independently, hydrogen or $C_1$—$C_4$-alkyl, and
- n is a number from 2 to 10.

10. A composition as set forth in claim 9, wherein said polymer is a polyurethane.

11. A composition as set forth in claim 10, wherein Ar is a $C_1$—$C_4$-alkoxyphenyl radical.

12. The composition as set forth in claim 11. wherein Ar is p-methoxyphenyl.

13. The composition as set forth in claim 9, wherein Ar is p-methoxyphenyl, n is 2 and $R^1$ is a dihydric polyol.

14. The composition of claim 13, wherein the dlhydric polyol is cyclohexane dimethanol.

15. A method as set forth in claim 1, wherein said polyurethane/stabilizer combination is formed into a foam.

16. The composition of claim 13, wherein the dihydric polyol is 1,4-butanediol.

17. A composition comprising:
a polyurethane or polycarbonate polymer; and
0.01 to 5% by weight, based on the weight of said organic material, of a 3-arylacrylic ester of formula I:

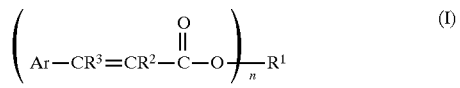 (I)

where
- Ar is an aryl radical optionally substituted by one to three $C_1$—$C_4$-alkyl groups $C_1$—$C_4$-alkoxy groups, hydroxyl groups phenoxy groups, amino groups which can be mono- or disubstituted by $C_1$—$C_4$-alkyl groups, or halogen atoms, nitro groups or a methylenedioxy group, said substituents being identical or different,
- $R^1$ is the residue of an n-hydric aliphatic polyol having, up to 20 carbon atoms, where the carbon chain can be interrupted by up to 9 non-adjacent ether oxygen atoms, or of an n-hydric cyclo-aliphatic polyol having 5 to 20 carbon atoms in which ring carbon atoms can also be replaced by non-adjacent ether oxygen atoms,
- $R^2$ and $R^3$ are each independently, hydrogen or $C_1$—$C_4$-alkyl, and
- n is a number from 2 to 10.

* * * * *